United States Patent [19]
Casillas

[11] 3,986,262
[45] Oct. 19, 1976

[54] VARIABLE AIR ACTUATED CONTROL UNIT FOR ELECTRICAL DENTAL HANDPIECES

[75] Inventor: Cecil J. Casillas, Culver City, Calif.

[73] Assignee: Progressive Machine Products, Inc., Los Angeles, Calif.

[22] Filed: Feb. 19, 1974

[21] Appl. No.: 443,374

[52] U.S. Cl. ................................................ 32/22
[51] Int. Cl.² .................................... A61C 19/02
[58] Field of Search ............. 32/26, 27, 28; 336/30; 73/398

[56] References Cited
UNITED STATES PATENTS

| | | | |
|---|---|---|---|
| 3,568,318 | 3/1971 | Martin | 32/27 |
| 3,676,931 | 7/1972 | Pietschmann | 32/27 |
| 3,844,039 | 10/1974 | Fleer et al. | 32/22 |
| 3,902,247 | 9/1975 | Fleer et al. | 32/22 |

Primary Examiner—Robert Peshock
Attorney, Agent, or Firm—Keith D. Beecher

[57] ABSTRACT

A control unit is provided for a plurality of dental handpieces of the electrically energized type, which includes individual arms for supporting the handpieces, and which selectively directs the flow of pressurized air to the handpieces, so that high pressure driving air may be supplied to a selected handpiece as it is removed from its supporting arm. The air pressure is controlled by a common controller which may be of the usual foot operated type in general use in most dental offices, so that the speed of the selected handpiece may be controlled. The unit includes a pressure-sensitive electrical impedance of each of the electrical handpieces which responds to the pressurized air from the controller as the corresponding electrical handpiece is selected to control the flow of electrical energy to the selected handpiece.

3 Claims, 4 Drawing Figures

VARIABLE AIR ACTUATED CONTROL UNIT FOR ELECTRICAL DENTAL HANDPIECES

BACKGROUND OF THE INVENTION

U.S. Pat. No. 3,755,899 describes a control unit for supporting and selectively distributing high pressure air to a plurality of high-pressure air-driven dental handpieces. An important objective of the present invention is to provide a similar type of control unit for supporting the electrically energized type of handpieces, and which selectively supplies high-pressure air from a common controller to pressure-sensitive impedance elements which control the handpieces. This permits the electrical handpieces to be interfaced in the control unit and used, either in conjunction with, or as a replacement for, the air-driven type of handpieces, all of which are controlled by the common air pressure controller.

The term "dental handpiece" as used herein is not intended to be limited to the rotating devices such as drills and burnishers, but is also intended to embrace a wide variety of dental devices such as vibrators, ultrasonic scaling devices, scalpels, electrosurgery devices, fiber optics and other lighting devices, and the like.

The control of the present invention permits such electrical dental handpieces to be interfaced in a common control with the air pressure type, and all may be controlled by a common air pressure controller. In the case of the electrically energized devices, the air pressure from the controller is used to control a pressure-sensitive impedance which, in turn, controls the electrical energy supplied to the selected handpiece.

DETAILED DESCRIPTION OF THE ILLUSTRATED EMBODIMENT

Figure 1:
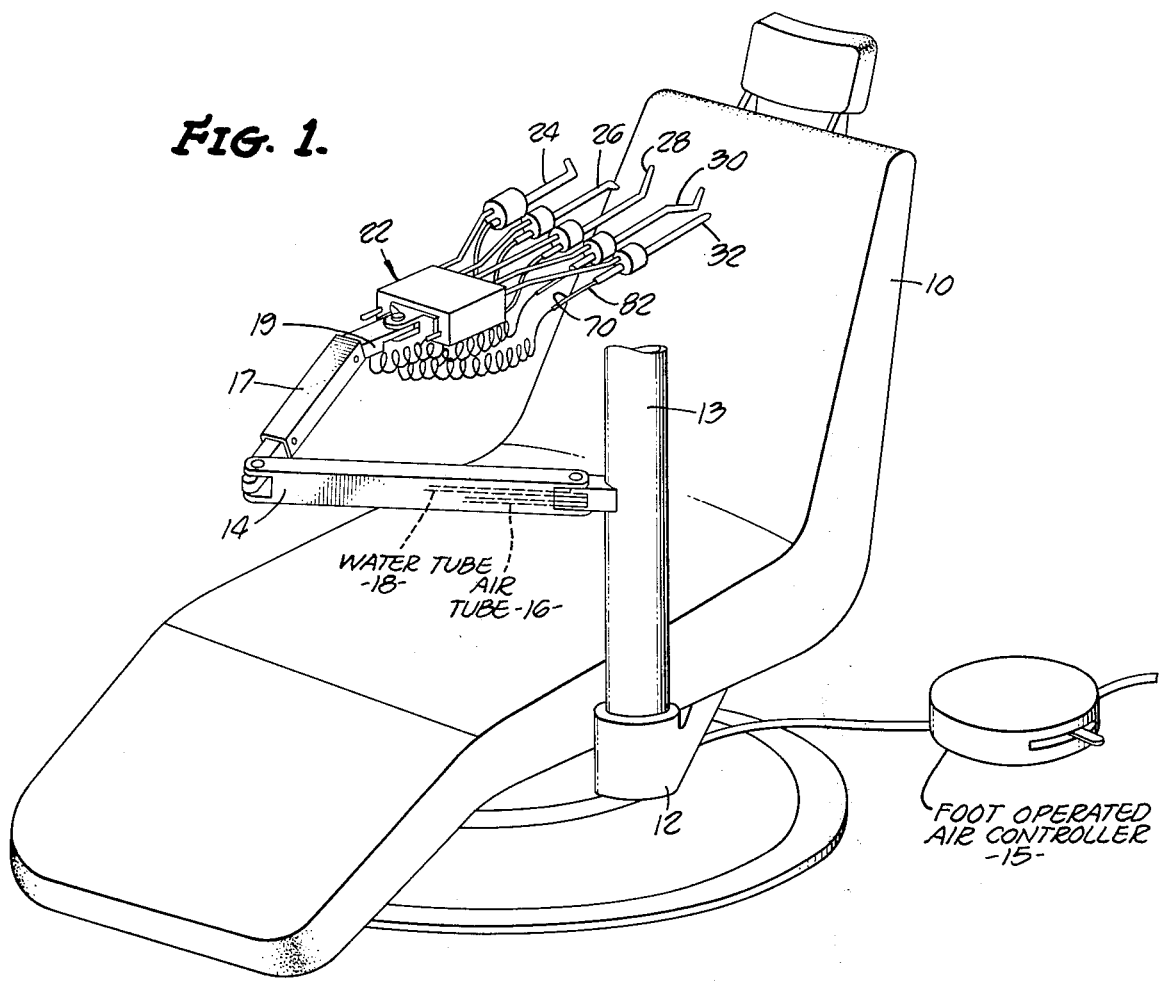
FIG. 1 is a perspective representation of a dental console which may be constructed to incorporate a control unit embodying the concepts and features of the present invention.
Figure 2:
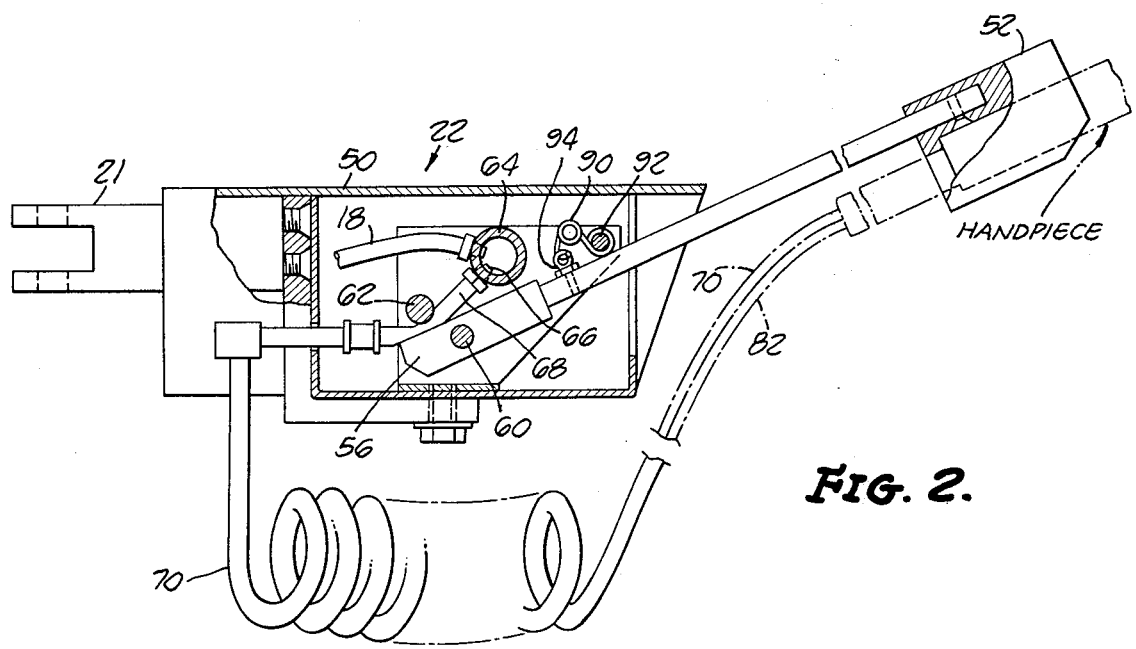
FIG. 2 is a side section of the control unit of FIG. 1, on an enlarged scale.

The representations of FIGS. 1 and 2 are generally similar to those of U.S. Pat. No. 3,755,899 referred to above. As shown in FIG. 1, a console incorporating the control unit of the invention is mounted on a dental chair 10 by means of an upright hollow tubular member 12. The console includes an upright hollow standard 13 which is fitted into the tubular member 12. A horizontal hollow arm 14 is pivotally coupled at one end to the upright standard 13. Further hollow arms 17 and 19 are hinged to the distal end of the arm 14 and to one another to provide vertical adjustment.

A flexible air tube 16 and a flexible water tube 18 extend up the hollow interior of the standard 12 and along the hollow interiors of the arms 14, 17 and 19. These tubes 16 and 18 are coupled to appropriate sources of water and compressed air, and the pressurized flow of these fluids through the respective flexible tubes is controlled by the dentist, by appropriate means, such as by a foot valve controller 15.

The tubes 16 and 18 pass from the arm 14 through the hollow interiors of the arms 17 and 19 to a control unit 22. The control unit 22, which incorporates the concepts of the invention, is mounted on the distal end of the arm 19, as shown in FIG. 1. The control unit 22 supports a plurality of dental handpieces 24, 26, 28, 30 and 32. These handpieces, for example, may in some instances be high-speed air-driven drills, or other air-driven devices, and in some instances the handpieces may be electrically energized, as will be described. The flow of pressurized air and/or water to a selected handpiece is controlled by the dentist, by flipping up the arm on which the particular handpiece was supported on the control unit 22, after the handpiece has been removed.

Details of the control unit 22 are shown, for example, in FIG. 2. The control unit includes a housing or frame 50 having, in the illustrated embodiment, a generally rectangular configuration. A plurality of brackets are supported in the control unit 22, each consisting of a handpiece holder 52, an elongated arm 54 and a pinch-block 56. As shown, each pinch-block 56 is attached to one end of its corresponding arm 54, and each holder 52 is attached to the other end. The holders 52 each has a generally tubular configuration with a longitudinally open top to permit a corresponding handpiece to be removably supported in the holder. The pinch-blocks 56 are pivotally mounted adjacent to one another in the frame 50 on a pivot rod 60. The pivot rod 60 is mounted on the frame, and it extends transversely across the frame. A pinch-bar 62 is also mounted on the frame, and it also extends across the frame adjacent to the pivot rod 60. The control unit shown in FIG. 2 is similar to the control unit shown and described in U.S. Pat. No. 3,755,899, and is such that when a handpiece holder 52 is moved to a down position, the corresponding pinch-block 56 rocks on the pivot arm 60 and moves against the pinch-bar 62.

An air manifold 64 is also mounted on the frame 50, and the air tube 18 is coupled to the manifold so that compressed air may be supplied to the manifold. The manifold 64 has a plurality of outlets 66, and flexible tubes, such as the tube 68 may be coupled to the respective outlets to supply the pressurized air to the various handpieces, by way, for example, of further tubes 70. Each tube 68 passes across the face of a corresponding pinch-block 56, and between the pinch-block and the pinch-bar 62.

Whenever a handpiece holder 52 is held in its down position, the corresponding pinch-block 56 pinches the flexible tube 68 against the pinch-bar 62 to prevent air from being transmitted to the corresponding handpiece. On the other hand, whenever a holder 52 is flipped to its up position, its pinch-block 56 is moved away from the pinch-bar 62, so that the compressed air may flow freely to the selected handpiece.

Each of the bracket arms 54 is connected to an over-center spring 90. Each spring 90 permits the corresponding arm 54 to be set to an up position or to a down position, and to be maintained in that position. Each spring 90 has one end attached to a pivot pin 92, and each has its other end connected to a bracket 94 mounted on the arm 54.

Figure 3:
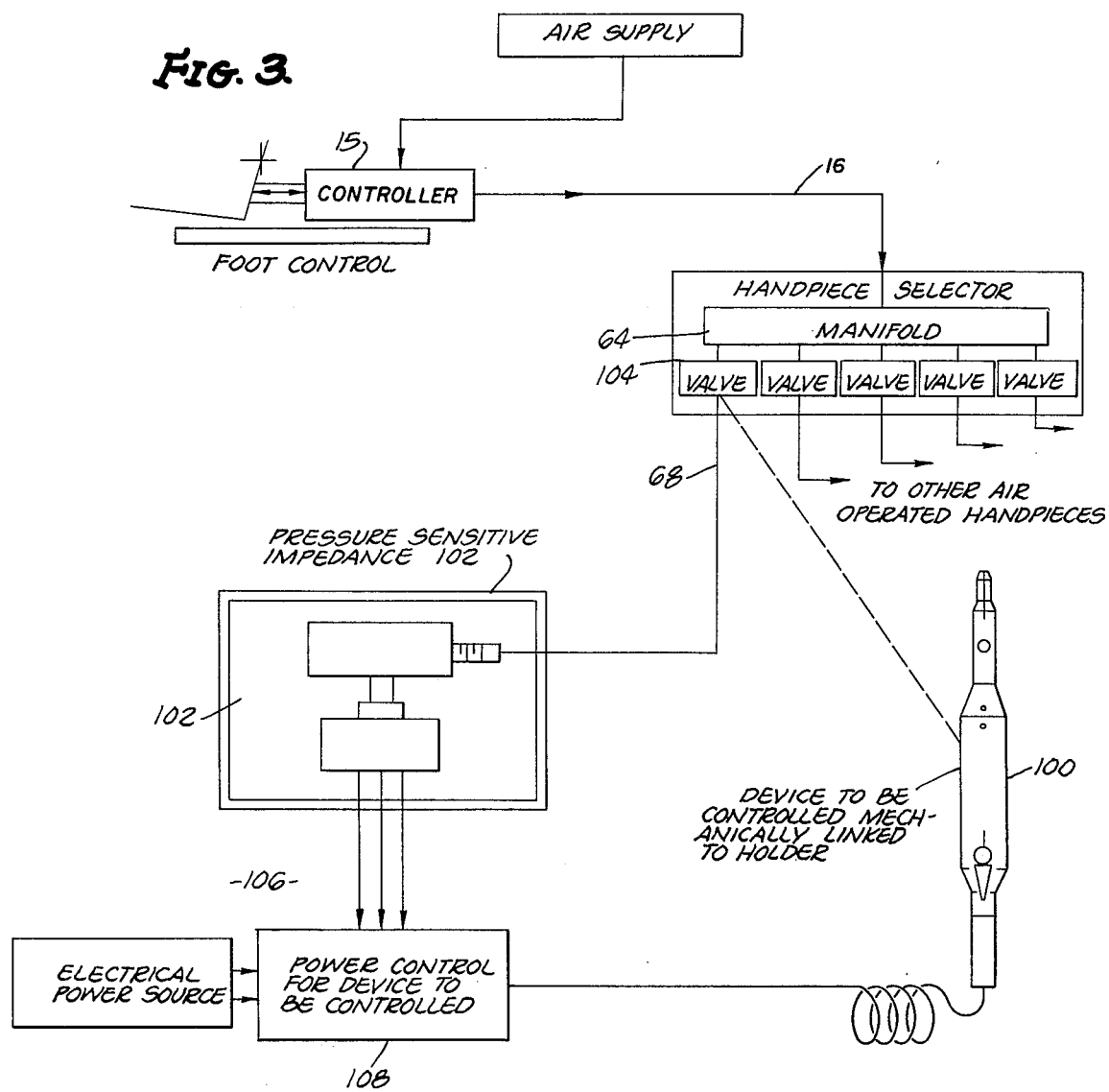
FIG. 3 is a schematic block diagram showing the operation of the control unit of the invention.

As mentioned above, the control unit of the present invention permits electrically operated handpieces to be interfaced on the common control unit with the high-pressure air-driven type. Each such electrically operated handpiece, designated 100 in FIG. 3 is controlled by a pressure-sensitive impedance 102 mounted in the control unit. As described above, the handpiece selector portion of the control unit 22 of FIG. 1 includes a manifold 64 which receives pressurized air through a flexible tube 16 from the foot valve controller 15. The manifold is selectively coupled to the various handpieces as the different pinch valves are selectively operated.

For example, should a valve 104 be operated by the selection of the handpiece 100, pressurized fluid is then supplied through the corresponding flexible tube 68 to the pressure-sensitive impedance 102, instead of directly to the handpiece, as is the case with the air-operated handpieces. The pressure-sensitive impedance 102, in turn, controls the amount of power supplied from the electrical power source 106 to the handpiece 100 through any appropriate electrical control circuit 108.

Figure 4:
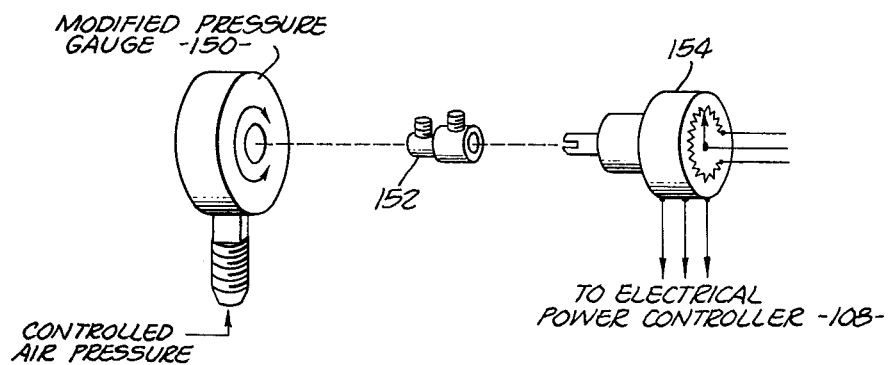
FIG. 4 is a schematic representation of one type of pressure-sensitive impedance element which may be used in the control unit of FIG. 3 to control the electric power supplied to an electrically operated handpiece.

The pressure-sensitive impedance 102 may take the form shown in FIG. 4, in which the tube 68 is coupled to a modified pressure gage 150 which is coupled through a collar 152 to a variable potentiometer 154. The leads from the potentiometer are connected to the electrical power controller 108. It is apparent that other impedance elements, such as capacitance or inductance elements may be controlled to effectuate the desired electrical power control. It is also evident that other types of pressure-sensitive impedances may be used, such as diaphragm types, piston types, or solid state types.

The invention provides, therefore, an improved control unit which includes pressure-sensitive impedance elements to permit electrically operated handpieces to be interfaced with air operated handpieces on a single control unit, and all the handpieces to be controlled by a common air pressure controller.

While a particular embodiment of the invention has been shown and described, modifications may be made. It is intended in the claims to cover the modifications which come within the spirit and scope of the invention.

What is claimed is:

1. A control unit for supporting a plurality of fluid-driven and electrically operated dental handpieces, including: a plurality of pivotally mounted individual bracket means for removably supporting the fluid-driven and electrically operated dental handpieces; a manifold; a plurality of individual tubes extending from the manifold; individual valve means operated by the respective bracket means and coupled to respective ones of the tubes to permit fluid flow through a corresponding tube when a handpiece is removed from its bracket means; a common tube coupling a source of fluid to the manifold for supplying fluid to the manifold; a manually operated controller coupled to the common tube for controlling the amount of fluid fed from the source to the manifold; means coupling the fluid-driven handpieces to corresponding ones of the individual tubes; an electrical power circuit connected to the electrically operated handpieces; a pressure-sensitive electrical impedance connected to the electrical power circuit for controlling the amount of electrical power supplied to a corresponding one of the electrically operated handpieces; and means coupling a corresponding one of the individual tubes to the pressure-sensitive impedance.

2. The control unit defined in claim 1, in which said individual tubes extending from the manifold are flexible tubes, and in which said individual valve means are pinched valves respectively engaging corresponding ones of the flexible tubes.

3. The control unit defined in claim 1, in which said manually operated controller is of the foot operated type.

* * * * *